(12) United States Patent
Schmid et al.

(10) Patent No.: US 8,624,229 B2
(45) Date of Patent: Jan. 7, 2014

(54) ORGANIC ELECTRONIC DEVICE AND DOPANT FOR DOPING AN ORGANIC SEMICONDUCTING MATRIX MATERIAL

(75) Inventors: Guenter Schmid, Hemhofen (DE); Jan Hauke Wemken, Nuremberg (DE); Marina A. Petrukhina, Schenectady, NY (US)

(73) Assignee: OSRAM Opto Semiconductors GmbH, Regensburg (DE)

( * ) Notice: Subject to any disclaimer, the term of this patent is extended or adjusted under 35 U.S.C. 154(b) by 320 days.

(21) Appl. No.: 12/884,683

(22) Filed: Sep. 17, 2010

(65) Prior Publication Data
US 2011/0089408 A1    Apr. 21, 2011

Related U.S. Application Data

(60) Provisional application No. 61/243,927, filed on Sep. 18, 2009.

(51) Int. Cl.
*H01L 29/08*    (2006.01)

(52) U.S. Cl.
USPC ............................................. 257/40; 438/99

(58) Field of Classification Search
USPC .................. 257/40, E51.027; 438/22, 34, 99
See application file for complete search history.

(56) References Cited

U.S. PATENT DOCUMENTS

| | | | |
|---|---|---|---|
| 2009/0001360 A1* | 1/2009 | Nakayama | 257/40 |
| 2009/0212280 A1* | 8/2009 | Werner et al. | 257/40 |

OTHER PUBLICATIONS

Bird, M. J., et al., "The Crystal and Molecular Structure of Anhydrous Copper Butyrate," Structure of Anhydrous Copper Butyrate, 1972, pp. 242-246.

Troyanov, S. I., et al., "Crystal Structure of Copper(II) Carboxylates: Anhydrous $CU_2(i\text{-}C_4H_9COO)_4$ and the Adduct $CU_2(Me_3CCOO)_4 2Me_3CCOOH$," 1992, pp. 907-912, Plenum Publishing Corporation.

Cotton, F. A., et al., "Syntheses and Crystal Structures of "Unligated" Copper(I) and Copper(II) Trifluoroacetates," 20110, pp. 6072-6079, American Chemical Society.

Kushner, K., et al., "The Synthesis of Copper II Carboxylates Revisited," In the Laboratory, Journal of Chemical Education, Jul. 2006, pp. 1042-1045, vol. 83, No. 7.

Sevryugina, Y., et al., "Tetranuclear Copper(1) Clusters: Impact of Bridging Carboxylate Ligands on Solid State Structure and Photoluminescence," Chemical Communications, The Royal Society of Chemisty, 2007, pp. 3853-3855.

Sevryugina, Y., et al., "The First Hexanuclear Copper(I) Carboxylate: X-ray Crystal Structure and Reactivity in Solution and Gas-Phase Reactions," Inorganic Chemisty Article, 2007, pp. 7870-7879, vol. 46, No. 19, American Chemical Society.

Sevryugina, Y., et al., "X-Ray Structure and Photoluminescence of copper(I) 2,6-bis(trifluoromethyl)benzoate," Inorganica Chimica Acta, ScienceDirect, 2007, pp. 3103-3107, Elsevier.

(Continued)

*Primary Examiner* — Julio J Maldonado
*Assistant Examiner* — Robert Bachner
(74) *Attorney, Agent, or Firm* — Slater & Matsil, L.L.P.

(57) ABSTRACT

An organic electronic device includes a substrate, a first electrode arranged on the substrate, at least a first functional organic layer arranged on the first electrode and a second electrode arranged on the first functional organic layer. The first functional organic layer includes a matrix material and a p-dopant with regard to the matrix material, wherein the p-dopant includes a copper complex containing at least one ligand.

14 Claims, 5 Drawing Sheets

(56) References Cited

OTHER PUBLICATIONS

Sevryugina, Y., et al., Breaking Infinite $Cu^1$ Carboxylate Helix Held by Cuprophilicity into Discrete $Cu_n$ Fragments (n=6, 4, 2), 2008, pp. 219-229, Wiley-VCH Verlag GmbH & Co.

Sevryugina, Y., et al., In Situ Synthesis and Crystal Growth of Copper(I) Carbonyl Trifluoroacetate: A dinuclear $[CU_2(O_2CCF_3)2(CO)_2]$ Core Structured Confirmed, 2009, pp. 229-232.

Endo, J., et al., "Organic Electroluminescent Devices with a Vacuum-Deposited Lewis-Acidic-Doped Hole-Injecting Layer," Japanese Journal of Applied Physics, vol. 41, Part 2, No. 3B, Mar. 15, 2002, pp. L358-L360.

Gao, W., et al., "Controlled p doping of the hole-transport molecular material N,N'-diphenyl-N,N'-bis(1-naphthyl)-1,1'-biphenyl-4,4'-diamine with tetrafluorotetracyanoquinodimethane," Journal of Applied Physics, vol. 94, No. 1, Jul. 1, 2003, 8 pages.

Harada, K., et al., "Organic Homojunction Diodes with a High Built-in Potentional: Interpretation of the Current-Voltage Characteristics by a Generalized Einstein Relation," Phyiscal Review Letters, vol. 94, Article 036601, Jan. 28, 2005, 4 pages.

He, G., et al., "High-efficiency and low-voltage p-i-n. electrophosphorescent organic light-emitting diodes with double-emission layers," Applied Physics Letters, vol. 85, No. 17, Oct. 25, 2004, pp. 3911-3913.

He, G., et al., "Very high-efficiency and low voltage phosphorescent organic light-emitting diodes based on a p-i-n junction," Journal of Applied Physics, vol. 95, No. 10, May 15, 2004, 5 pages.

Kurata, T., "Charge-Transporting Property of Polymer Films Doped with Organic Stable Radicals," Journal of Photopolymer Science and Technology, vol. 16, No. 2, 2003, 2 pages.

Zhou, X., "Enhanced Hole Injection into Amorphous Hole-Transport Layers of Organic Light-Emitting Diodes Using Controlled p-Type Doping," Advanced Functional Materials, vol. 11, Issue 4, Aug. 2001, pp. 310-314.

Zhou, X., "High-efficiency electrophosphorescent organic light-emitting diodes with double light-emitting layers," Applied Physics Letters, vol. 81, No. 21, Nov. 18, 2002, 2 pages.

Zhou, X., "Low-voltage inverted transparent vacuum deposited organic light-emitting diodes using electrical doping," Applied Physics Letters, vol. 81, No. 5, Jul. 29, 2002, 3 pages.

* cited by examiner

ORGANIC ELECTRONIC DEVICE AND DOPANT FOR DOPING AN ORGANIC SEMICONDUCTING MATRIX MATERIAL

This application claims the benefit of U.S. Provisional Application No. 61/243,927, filed on Sep. 18, 2009, entitled "Organic Electronic Device and Dopant for Doping an Organic Semiconducting Matrix Material," which application is hereby incorporated herein by reference.

TECHNICAL FIELD

The disclosure relates to an organic electronic device that contains a copper complex as a p-dopant for doping an organic semiconducting matrix material used for a functional organic layer comprised in the organic electronic device. The disclosure further relates to a dopant for doping an organic semiconducting matrix material wherein the dopant is a polynuclear copper complex.

BACKGROUND

It is known to modify organic semiconductors with regard to their electrical characteristics, especially their electrical conductivity, by doping them. The doping leads to an increase in the conductivity of charge transport layers, thus reducing ohmic losses, and to an improved passage of the charge carriers within the organic layers.

Aspects of the invention solve the problem of providing p-dopants for doping an organic semiconducting matrix material, especially for manufacturing organic electronic devices, preferably dopants which cause an effective increase in the number of charge carriers in the matrix material.

An organic electronic device according to the disclosure comprises a substrate, a first electrode arranged on the substrate, at least a first functional organic layer arranged on the first electrode and a second electrode arranged on the first functional organic layer. The first functional organic layer of this device comprises a matrix material and a p-dopant with regard to the matrix material; the p-dopant comprises a copper complex containing at least one ligand L of the following formula:

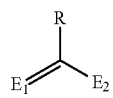

wherein $E_1$ and $E_2$ may be the same or different and represent oxygen, sulfur, selenium or NR', wherein R represents a substituted or unsubstituted hydrocarbon, which may be branched, linear or cyclic, and wherein R' represents hydrogen or a substituted or unsubstituted, branched, linear or cyclic hydrocarbon; R' may also be connected with R.

Thereby, the fact that one layer or one element is arranged or applied "on" or "above" another layer or another element can mean here and hereinafter that one layer or one element is arranged in direct mechanical and/or electrical contact on the other layer or the other element. Furthermore, it can also mean that one layer or one element is arranged indirectly on or respectively above the other layer or the other element. In this case, further layers and/or elements can then be arranged between one and the other layer.

Thereby, the first functional organic layer can particularly be selected from the group comprising one or a plurality of electroluminescent layers (EL), electron blocking layers (EBL), hole transport layers (HTL) and hole injection layers (HIL). Any further functional organic layer can be selected from the group comprising one or a plurality of electron injection layers (EIL), electron transport layers (ETL), hole blocking layers (HBL), electroluminescent layers (EL), electron blocking layers (EBL), hole transport layers (HTL) and/or hole injection layers (HIL). The recombination of electrons and holes leads to the electroluminescence. Individual layers can also have functionalities of a plurality of the aforementioned layers. Thus, a layer can serve, for example, as HIL and as HTL or as EIL and as ETL.

The functional layers can comprise organic polymers, organic oligomers, organic monomers, organic small, non-polymeric molecules ("small molecules") or combinations thereof.

According to the disclosure it was observed that copper complexes with ligands L being carboxylates, homologues of carboxylates and the respective amides and amidinates may improve the whole transport in a functional organic layer, i.e., the hole-conductivity of the layer is increased by the dopant. If the organic electronic device is a radiation emitting device (for example, an OLED), surprisingly, these dopants usually do not quench radiation emission. Usually, particularly the copper(I) complexes even exhibit luminescence by themselves and can help to detect loss channels in the device fabrication. It was observed for the first time that a radiation emitting compound can also be used to increase hole-conductivity. A further advantage of the present copper complexes is that the starting materials for these complexes are generally of low cost.

The copper complex of the present disclosure serves as a p-dopant; therefore, the copper complex is a metal organic acceptor compound with respect to the matrix material of the first functional organic layer. Normally, the copper complex is a neutral (electron-poor) complex and has at least one organic ligand L, without being restricted to that.

The copper complexes in the first functional organic layer may be isolated molecules. However, usually these copper complexes are connected to molecules comprised in the matrix material by chemical bonds (i.e., the molecules comprised in the matrix material serve as ligands coordinating to the copper complex). Normally, the copper atom (or all of the copper atoms) are coordinated to organic ligands only. However, the organic ligands may possess suitable functional groups which allow linking to form an oligomer or polymer.

In an embodiment the ligand L may be at least bidentate, tridentate or tetradentate, and may particularly contain at least one or two moieties $C(=E_1)E_2$ with at least one, two, three, four or more of the donor atoms $E_1$ and $E_2$ of the ligands coordinating to the copper atoms of the present p-dopant. Usually all donor atoms $E_1$ and $E_2$ coordinate to the copper atoms of the present complex. The $C(=E_1)E_2$-moiety usually has one negative charge. However, in theory the not deprotonated carboxylic acid (its homologues and the respective amides and amidinates) can also serve as a ligand. In general, the ligand L of the present disclosure contributes negative charges to the complex (i.e., one negative charge per $CE_2$ group).

According to an embodiment, the copper complex of the present disclosure is (in the state where no matrix molecule coordinates to the copper atom) a homoleptic complex where only ligands L are coordinated to the central copper atom. Further, the copper complex (particularly the copper complex containing only ligands L) is often, as long as no molecule of the matrix material coordinates to the central copper atom, complex with square planar or linear molecular geometry, particularly if copper-copper interactions are disregarded. Upon coordination of a matrix molecule the geometry is usually altered and, for example, a pentagonal-bipyramidal coordination geometry or a square pyramidal molecular geometry results. Usually, in all alternatives described in this paragraph the copper complex is still, as mentioned before, a neutral complex.

It shall be understood that previous definitions of the copper complexes and/or ligands apply to mononuclear copper complexes but also to polynuclear copper complexes. In polynuclear copper complexes the ligand L may bind to only one copper atom and also to two copper atoms (i.e., bridging two copper atoms). If ligands L are contained which are tridentate, tetradentate or multidentate ligands, also more than two copper atoms of the polynuclear copper complex may be bridged. In the case of polynuclear copper complexes copper-copper bonds may exist between two or more copper atoms. However, particularly as far as copper (I) complexes are concerned, usually no copper-copper bonds (of the copper complexes without coordinating molecules of the matrix) are observed. This may be proven by x-ray spectroscopy and by absorption spectroscopy (which shows a square planar surrounding of the copper atoms, i.e., a copper atom surrounded by four organic ligands, particularly four ligands L or copper complexes with two coordinated ligands, particularly two ligands L, with a linear geometry of the complex). Copper(I) complexes often show cuprophilic Cu—Cu interactions; The Cu—Cu carboxylate bridged distances may very broadly vary from 2.5 to 3.2 Å.

If polynuclear copper complexes are used, the organic electronic device and in particular the first functional organic layer exhibits an improved lifetime. Presumably, charges transported via the first functional organic layer may cause a destabilizing effect with regard to the copper complex. If, however, more than one copper atom is present in the copper complex, the destabilizing effect is distributed on all copper-atoms. Therefore, polynuclear complexes usually show an improved stability compared to mononuclear complexes.

In an embodiment, the polynuclear copper complexes show a so-called "paddle-wheel" structure, particularly as far as copper (II) complexes are concerned. A paddle-wheel complex is a complex with usually two metal atoms, in the present case copper atoms, which are bridged by one, two, three, four or even more multidentate ligands, in the present case usually two or most often four ligands L. Usually the coordination mode of all ligands (with respect to the copper atoms) is almost identical so that, with respect to copper atoms and ligands L, at least one two-fold or four-fold rotation axis through two of the copper atoms contained in the polynuclear complex is defined. Square planar complexes often exhibit an at least four-fold rotation axis; linear coordinated complexes often show a two-fold rotation axis.

In an embodiment of the present application, the copper atom of the mononuclear complex or at least a part of the copper atoms (usually all copper atoms) of the polynuclear copper complex shows the oxidation state +2. In these complexes the ligands are mostly coordinated in a square planar geometry (in the state where no molecules of the matrix are coordinating to the copper atom).

In a further embodiment the copper atom in the mononuclear complex or at least a part of the copper atoms (usually all copper atoms) of the polynuclear complex are in the oxidation state +1. In those complexes the coordination mode of the copper atom is mostly linear (as long as no molecule of the matrix coordinates to the copper atom).

Complexes containing copper (II) atoms usually exhibit a better hole transport ability than complexes containing copper (I) atoms. Copper (I) complexes have a closed shell $d^{10}$ configuration. Therefore, the effect originates primarily form the Lewis acidity of the copper atom. Copper (II) complexes have a not closed $d^9$ configuration, thus giving rise to an oxidation behavior. Partial oxidation increases the hole density. On the other hand, complexes containing copper (I) atoms are often thermally more stable than corresponding copper (II) complexes.

In a preferred embodiment, the copper complex of the present disclosure (in the state where no molecules of the matrix are coordinated) is Lewis-acidic. A Lewis-acidic compound is a compound which acts as an electron pair acceptor. A Lewis-base, therefore, is an electron pair donator. The Lewis-acidic behavior of the present copper complexes is particularly related to the molecules of the matrix material. Therefore, the molecules of the matrix material usually act as a Lewis-base with respect to the Lewis-acidic copper complexes.

A Lewis-acidic complex according to the present disclosure may also be a complex as described before wherein a solvent molecule coordinates to the central copper atom at the free coordination site described before. However, particularly the tested copper complexes described in the examples below do not comprise a solvent molecule.

In the present disclosure the copper atom contains an open (i.e., a further) coordination site. To this coordination sites the coordination of a (Lewis-basic) compound, particularly an aromatic ring or a nitrogen atom of an amine component contained in the matrix material can coordinate (see the following schemes 1 and 2):

scheme 1

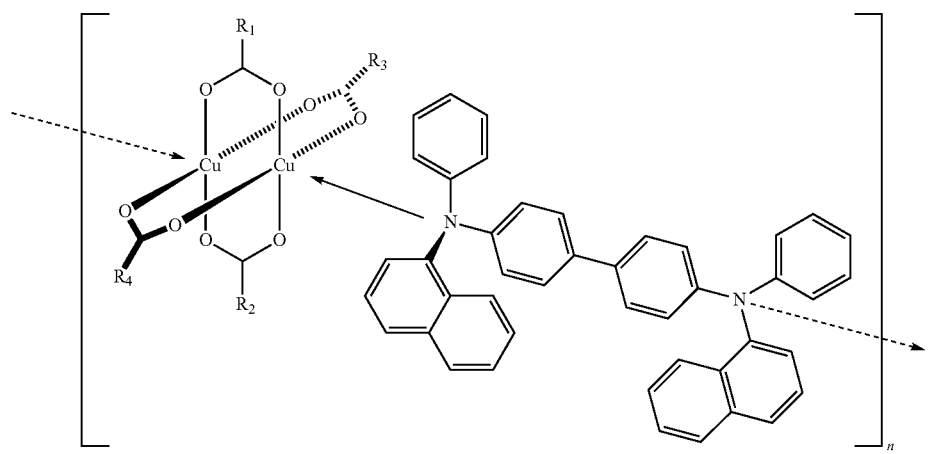

scheme 2

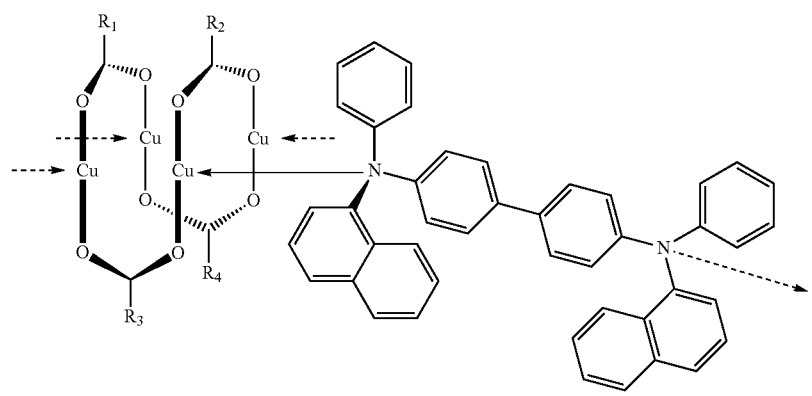

However, also other groups different from aromatic rings or amine nitrogen atoms are possible as far as aromatic ring systems are contained also hetero aromatic rings may coordinate to the copper atom. Often, a coordination of the nitrogen atom of an amine component is observed.

In an embodiment of the present disclosure, the ligand L coordinating to the copper atom contains a group R representing a substituted or unsubstituted hydrocarbon, which may be branched, linear or cyclic. The branched, linear or cyclic hydrocarbon may particularly contain 1-20 carbon atoms, for example, methyl, ethyl or condensed substituents (like decahydronaphthyl or adamantyl, cyclo-hexyl or fully or partly substituted alkyl-moieties). The substituted or unsubstituted aromatic groups R may, for example, be phenyl, biphenyl, naphthyl, phenanthryl, benzyl or a hetero aromatic residue, for example, a substituted or unsubstituted residue selected from the heterocycles depicted in the following:

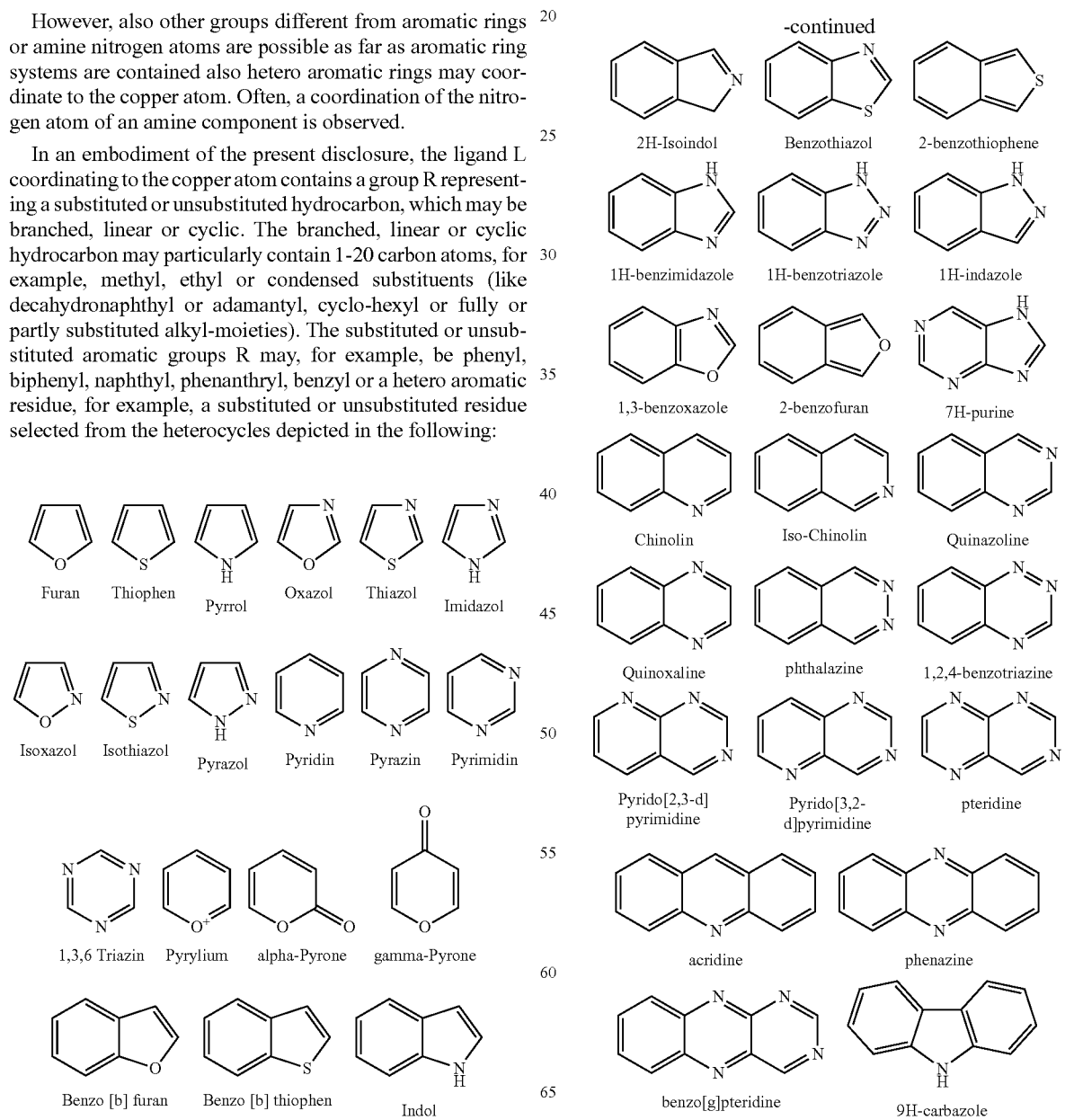

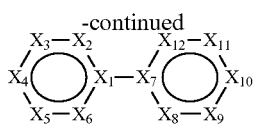

Bipyridin & Derivate
(0-2 X₁/Ring = N)

In a further embodiment of the present disclosure, the ligand L coordinating to the copper atom contains a group R representing an alkyl and/or aryl group wherein the alkyl, aryl or aralkyl group bears at least one electron withdrawing substituent. The copper complex may contain more than one type of carboxylic acids (mixed systems), amides and amidinates, wherein the word "type" refers on the one hand to the substituent R and on the other hand to the hetero atoms being connected to the copper.

An electron withdrawing substituent according to this disclosure is a substituent which reduces the electron density at the atom to which the electron withdrawing substituent is bound compared to the respective atom bearing a hydrogen atom instead of the electron withdrawing substituent.

The electron withdrawing groups may, for example, be selected from the group containing halogens (e.g., chlorine and particularly fluorine), nitro groups, cyano groups and mixtures of these groups. The alkyl and/or aryl group may bear exclusively electron withdrawing substituents, for example, the aforesaid electron withdrawing groups or hydrogen atoms as well as one or more electron withdrawing substituents.

If ligands L wherein the alkyl and/or aryl groups bear at least one electron withdrawing substituent are used, the electron density at the central atom (s) of the copper complex can be reduced; therefore, the Lewis-acidity of the copper complex can be increased.

The ligand L may, for example, be the anion of the following carbonic acids: $CHal_xH_{3-x}COOH$, particularly $CF_xH_{3-x}COOH$ and $CCl_xH_{3-x}COOH$, (wherein x represents an integer from 0 to 3 and Hal represents an halogen atom), $CR''_yHal_xH_{3-x-y}COOH$ (wherein x and y are integers and x+y=a number from 1 to 3 and wherein y is at least 1 and Hal represents a halogen atom); the substituent R" may be alkyl or hydrogen or an aromatic group, particularly phenyl; all groups described before for the residue R" may contain electron withdrawing substituents, particularly the electron withdrawing substituents mentioned before or a derivative of benzoic acid containing an electron withdrawing substituent (for example, ortho-, para- or meta-fluoro benzoic acid, ortho-, para- or meta-cyano benzoic acid, ortho-, para- or meta-nitro benzoic acid or benzoic acids bearing one or more fluorinated or perfluorinated alkyl groups, for example, a tri-fluoro methyl group. For example, the ligand L may be the anion of the following carbonic acid $R''—(CF_2)_n—CO_2H$ with n=1-20; R" stands for the same groups as listed above for R, particularly again a group bearing electron withdrawing moieties (for example, fully or partially fluorinated aromatic compounds). If the volatility of the ligand L is too high (which may occur, for example, if perflorinated acetates and propionates are used), the molecular weight and thus the evaporation temperature can be increased, without losing too much Lewis acidity with respect to the trifluoroacetate. Therefore, for example, fluorinated, particularly perfluorinated, homo- and heteroaromatic compounds can be used as moieties R and R", respectively. Examples are the anions of fluorinated benzoic acids:

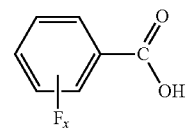

wherein the phenyl ring bears 1 to 5 fluorine substiutents (i.e., x=1-5). Particularly the following substituents, which are strong Lewis acids, (or the corresponding substituents bearing chlorine atoms instead of fluorine atoms) may be bound to the carboxylate group:

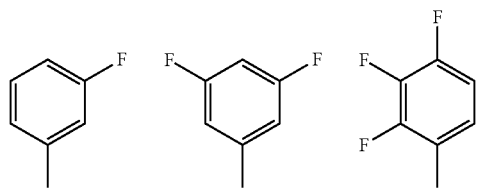

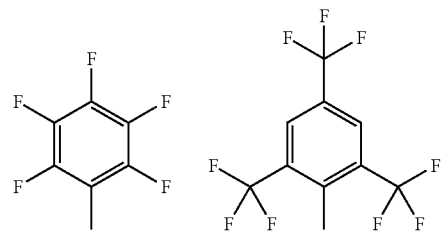

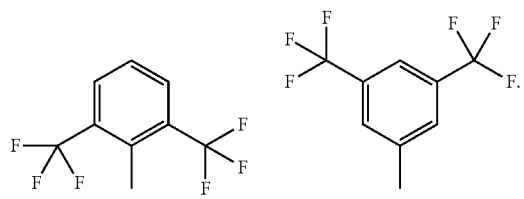

Furthermore, the anions of the following acid may be used as ligands:

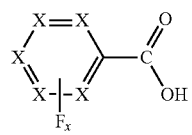

wherein X may be a nitrogen atom or a carbon atom bearing, for example, a hydrogen atom or a fluorine atom. According to an embodiment three Atoms X stand for N and two for C—F or C—H (triazine derivatives). Also the anions of the following acid may be used as ligands:

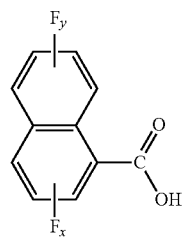

wherein the naphthyl ring bears 1 to 7 fluorine substiutents (i.e., y=0-4 and x=0-3 wherein y+x=1-7).

According to an embodiment, ligands L having the following structure may be used:

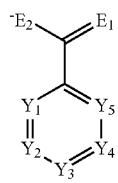

wherein $E_1$ and $E_2$ are defined as above, wherein $Y_1, Y_2, Y_3, Y_4$ and $Y_5$ represent the same or different groups or atoms and wherein $Y_1, Y_2, Y_3, Y_4$ and $Y_5$ are independently selected from the following atoms and/or groups: C—F, C—Cl, C—Br, C—NO$_2$, C—CN, N, C—N$_3$, C—OCN, C—NCO, C—CNO, C—SCN, C—NCS, and C—SeCN, particularly independently selected from the following atoms and/or groups C—F, C—NO$_2$, C—CN, and N. Thus, all ring members beside the C-Atom connected to the $CE_2^-$ group are selected from these atoms and/or groups. These ligands L may for example be selected from the following ligands:

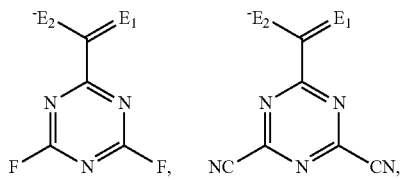

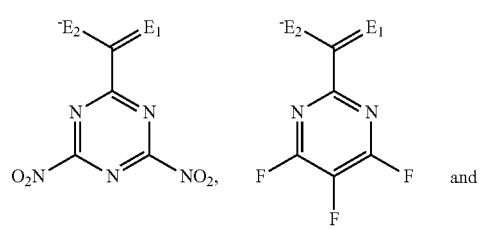

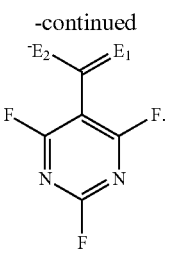

According to this embodiment also aromatic substituents R being different from substituents R deriving from six-membered rings, i.e., from phenyl are possible, for example, substituents R deriving from polycyclic aromats, for example, deriving from 1-nayphthyl and 2-naphthyl. These ligands L may, for example, be selected from the following ligands:

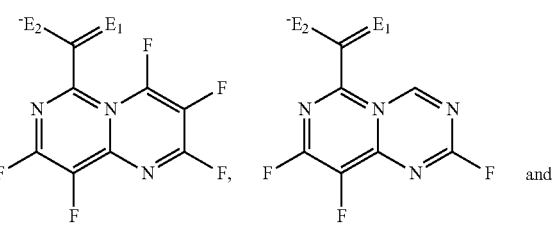

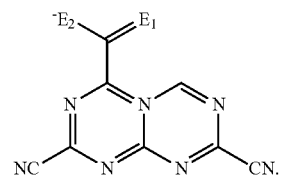

In particular, fluorine as electron withdrawing substituent is mentioned as copper complexes containing fluorine atoms in the coordinated ligands may be evaporated and deposited more easily. A further group to be mentioned is the trifluoromethyl group.

In a further embodiment of the present disclosure, the group R' (in the case of amidinates one or both of the groups R') is represented by a substituted or unsubstituted, branched, linear or cyclic hydrocarbon which bears at least one electron withdrawing substituent. This electron withdrawing substituent is defined as above with respect to the group R.

In an embodiment, the first functional layer is a hole-transport layer. The addition of the copper complex to the matrix material of the hole-transport layer results in an improved hole-transport compared to the matrix material containing no p-dopant. This improved hole-transport may be explained by the transfer of the hole (or a positive charge) from the molecules of the matrix material being coordinated to the copper complex to the copper atoms and vice versa. This transfer is depicted in the following scheme 3 containing several mesomeric structures of a copper (II) complex (the ligands L or any other ligands or additional copper atoms contained in the copper complex being omitted for the purpose of clarity).

scheme 3

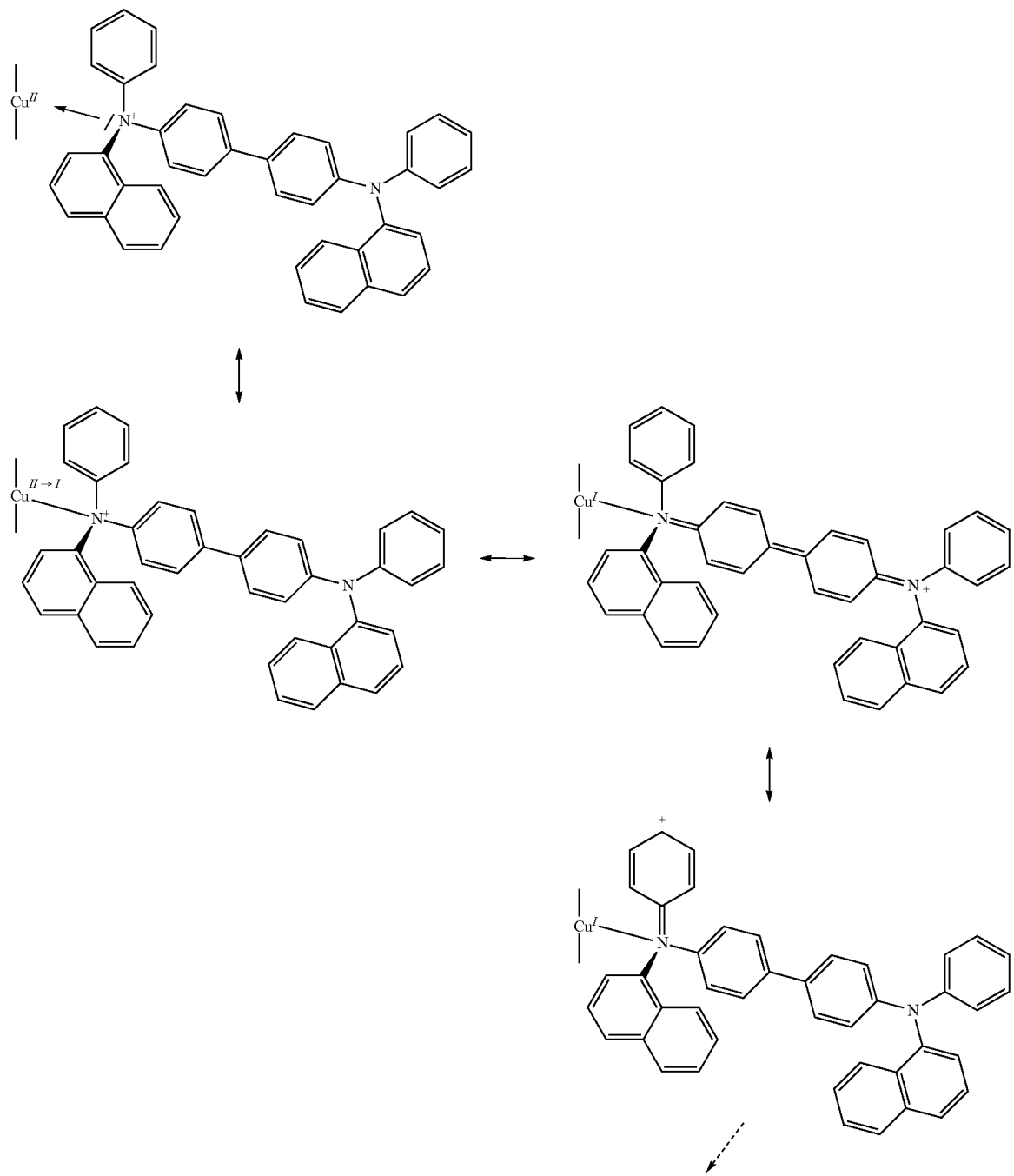

If the device according to the present disclosure is a radiation emitting device, usually no exciton blocking layers between the light emitting layer and the hole-transport layer acting as a first functional organic layer are necessary as no quenching occurs upon addition of the p-dopant to the hole-transport layer.

The matrix material of the hole-transport layer may be selected from one or more compounds of the following group consisting of NPB (N,N'-bis(naphthalen-1-yl)-N,N'-bis(phenyl)-benzidine, β-NPB (N,N'-bis(naphthalen-2-yl)-N,N-bis(phenyl)-benzidine), TPD (N,N'-bis(3-methylphenyl)-N,N'-bis(phenyl)-benzidine), N,N'-bis(naphthalen-1-yl)-N,N'-bis(phenyl)-2,2-dimethylbenzidine, Spiro-TPD (N,N'-bis(3-methylphenyl)-N,N'-bis(phenyl)-9,9-spirobifluorene), Spiro-NPB (N,N'-bis(naphthalen-1-yl)-N,N-bis(phenyl)-9,9-spirobifluorene), DMFL-TPD (N,N'-bis(3-methylphenyl)-N,N'-bis(phenyl)-9,9-dimethylfluorene, DMFL-NPB (N,N'-bis(naphthalen-1-yl)-N,N'-bis(phenyl)-9,9-dimethylfluorene), DPFL-TPD (N,N'-bis(3-methylphenyl)-N,N'-bis(phenyl)-9,9-diphenylfluorene), DPFL-NPB (N,N'-bis(naphth-1-yl)-N,N'-bis(phenyl)-9,9-diphenylfluorene), Sp-TAD (2,2',7,7'-tetrakis(m,n-diphenylamino)-9,9'-spirobifluorene), TAPC (di-[4-(N,N-ditolyl-amino)-phenyl]cyclohexane), Spiro-TTB (2,2',7,7'-tetra(N,N-di-tolyl)amino-spiro-bifluorene), BPAPF (9,9-bis[4-(N,N-bis-biphenyl-4-yl-amino)phenyl]-9H-fluorene), Spiro-2NPB (2,2',7,7'-tetrakis[N-naphthyl(phenyl)-amino]-9,9-spirobifluorene), Spiro-5 (2,7-bis[N,N-bis(9,9-spiro-bifluoren-2-yl)-amino]-9,9-spirobifluorene), 2,2'-Spiro-DBP (2,2'-bis[N,N-bis(biphenyl-4-yl)amino]-9,9-spirobifluorene), PAPB (N,N'-bis(phenanthren-9-yl)-N,N'-bis(phenyl)-benzidine), TNB (N,N,N',N'-tetra-naphthalen-2-yl-benzidine), Spiro-BPA (2,2'-bis(N,N-di-phenyl-amino)-9,9-spirobifluorene), NPAPF (9,9-Bis[4-(N,N-bis-naphth-2-yl-amino)phenyl]-9H-fluorene), NPBAPF (9,9-bis[4-(N,N'-bis-naphth-2-yl-N,N'-bis-phenyl-amino)-phenyl]-9H-fluorene), TiOPC (titanium oxide phthalocyanine), CuPC (copper phthalocyanine), F4-TCNQ (2,3,5,6-tetrafluor-7,7,8,8,-tetracyano-quinodimethane), m-MTDATA (4,4',4''-tris(N-3-methylphenyl-N-phenyl-amino)triphenylamine), 2T-NATA (4,4',4''-tris(N-(naphthalen-2-yl)-N-phenyl-amino)triphenylamine), 1T-NATA (4,4',4''-tris(N-(naphthalen-1-yl)-N-phenyl-amino) triphenylamine), NATA (4,4',4''-tris(N,N-diphenylamino) triphenylamine), PPDN (pyrazino[2,3-f][1,10] phenanthroline-2,3-dicarbonitrile), MeO-TPD (N,N,N',N'-tetrakis(4-methoxyphenyl)benzidine), MeO-Spiro-TPD (2,7-bis[N,N-bis(4-methoxy-phenyl)amino]-9,9-spirobifluorene), 2,2'-MeO-Spiro-TPD (2,2'-bis[N,N-bis(4-methoxy-phenyl)amino]-9,9-spirobifluorene), β-NPP(N,N'-di(naphthalen-2-yl)-N,N'-diphenylbenzene-1,4-diamine), NTNPB (N,N'-di-phenyl-N,N'-di-[4-(N,N-di-tolyl-amino) phenyl]benzidine) and NPNPB (N,N'-di-phenyl-N,N'-di-[4-(N,N-di-phenyl-amino)phenyl]benzidine).

In a further embodiment, the first functional layer of the organic electronic device of the present application may be an electron blocking layer. If the copper complexes according to the present disclosure were used in an electron blocking layer, even if matrix materials usually used for electron transport materials are contained, almost no electron conductivity was observed. As mentioned before, every matrix material used in electronic organic devices may be the matrix material of the first functional layer being an electron blocking layer, even electron transporting matrix materials. For example, the matrix material can be a matrix material usually used for electron blocking layers. The (electron conducting) matrix material can, for example, be selected from one or more of the materials of the group consisting of Liq (8-hydroxyquinolinolato-lithium), TPBi (2,2',2''-(1,3,5-benzinetriyl)-tris(1-phenyl-1-H-benzimidazole)), PBD (2-(4-biphenylyl)-5-(4-tert-butylphenyl)-1,3,4-oxadiazole), BCP (2,9-dimethyl-4,7-diphenyl-1,10-phenanthroline), BPhen (4,7-Diphenyl-1,10-phenanthroline), BAlq (bis-(2-methyl-8-quinolinolate)-4-(phenylphenolato)aluminum), TAZ (3-(4-biphenylyl)-4-phenyl-5-tert-butylphenyl-1,2,4-triazole), CzSi (3,6-bis(triphenylsilyle)carbazole), NTAZ (4-(naphthalen-1-yl)-3,5-diphenyl-4H-1,2,4-triazole), Bpy-OXD (1,3-bis[2-(2,2'-bipyridine-6-yl)-1,3,4-oxadiazo-5-yl]benzene), BP-OXD-Bpy (6,6'-bis[5-(biphenyl-4-yl)-1,3,4-oxadiazo-2-yl]-2,2'-bipyridyl), PADN (2-phenyl-9,10-di(naphthalen-2-yl)-anthracene), Bpy-FOXD (2,7-bis[2-(2,2'-bipyridine-6-yl)-1,3,4-oxadiazo-5-yl]-9,9-dimethylfluorene), OXD-7 (1,3-bis[2-(4-tert-butylphenyl)-1,3,4-oxadiazo-5-yl]benzene), HNBphen (2-(naphthalen-2-yl)-4,7-diphenyl-1,10-phenanthroline), NBphen (2,9-bis(naphthalen-2-yl)-4,7-diphenyl-1,10-phenanthroline), 3TPYMB (tris(2,4,6-trimethyl-3-(pyridin-3-yl)phenyl)borane) and 2-NPIP (1-methyl-2-(4-(naphthalen-2-yl)phenyl)-1H-imidazo[4,5-f][1,10] phenanthroline).

In a further embodiment, the first functional layer is an emission layer. Therefore, the first functional layer comprises a matrix material, the copper complex according to the disclosure and a light emitting material; alternatively, the first functional organic layer may comprise a light emitting matrix material and the copper complex. In theory, the first functional organic layer according to this embodiment may also contain a matrix material and the p-dopant (copper complex), wherein the p-dopant additionally serves as a light emitting substance. However, usually the intensity of the light emitted by the copper complexes according to the disclosure exhibits, with respect to the light emitting materials used for OLEDs known by the skilled person, are a relatively low intensity. Therefore, applications using the copper-complexes/p-dopants according to the disclosure as light emitting molecules will usually contain a further emitter layer and the emitter layer containing the copper complex will only serve for changing the spectrum (or the color) of the emitted radiation.

As already outlined before, the matrix material of the first functional organic layer comprises an organic compound or consists of this organic compound. Usually, at least a part of this organic compound coordinates to the copper complex (i.e., the p-dopant according to the disclosure). Therefore, not all molecules of the organic material of the matrix material coordinate to copper atoms. However, one and the same organic compound may also coordinate to two or sometimes even more copper atoms. If the organic compound contained in the matrix material of the first functional organic layer contains, as described before, two or more coordination sites a part of which coordinates two copper atoms catenarian structures or netlike structures of a plurality of the copper complexes (as defined in claim 1) and a plurality of organic molecules may be formed.

The coordination of the organic compound may result from interactions of σ-electrons and/or π-electrons of the organic compound with the copper atom. Usually the hole-transport ability is improved if the number of catenarian or netlike structures in the first functional layer is increased. Therefore, also the increase of possible coordination sites usually leads to an increase of hole-transport as the formation of netlike structures or catenarian structures is favored.

Furthermore, also the structure of the copper complex has an influence on the propensity of coordination of the organic compound. The smaller the substituents R of the ligand L are, the less shielded the free coordination site of the copper atom is and the easier a coordination site of the organic compound will coordinate to the copper atom. Therefore, substituents R being linear alkyl groups may be used, if a "deshielding" of the copper atom is desired.

In an embodiment, the amount of p-dopant/copper complex contained in the first organic functional layer is 50% by volume with respect to the matrix material, for example, the amount of the p-dopant may be 30% by volume or less. Often the amount of the p-dopant with respect to the matrix material will be at least 5% by volume and 15% by volume at the most. The concentration by volume can easily be observed by comparison of evaporated matrix material and evaporated p-dopant if the first functional organic layer is produced by simultaneous evaporation of matrix and p-dopant (the layer thickness for and after evaporation can be measured). A variation of the amount of p-dopant can easily be realized by changing the temperature used for evaporation of the source of p-dopant and matrix material. In embodiments where no evaporation of the matrix material and the p-dopant is used, the respective proportion of p-dopant in weight percent (calculated by multiplication with the density of the respective material) can easily be calculated.

The organic electronic device according to the disclosure may, in particular, be a radiation emitting device, for example, an organic light emitting diode (OLED). The organic electronic device may further be, for example, an organic field effect transistor, an organic solar cell, a photo detector, a display or in general also an opto-electronic component. An organic electronic device containing the p-dopants/copper complexes according to the disclosure serving as components improving hole-transport is particularly suited for organic electronic devices wherein the efficiency strongly depends on a good hole-transport. For example, in an OLED, the generated luminescence is directly dependent on the number of formed excitons. The number of excitons is directly dependent on the number of recombining holes and electrons. A good hole-transport (as well as electron transport) gives rise to a high rate of recombination and, therefore, to a high efficiency and luminescence of the OLED. Furthermore, the power efficiency increases, when a voltage drop over the transport layers decreases. If the conductivity of the transport layers is about 3 to 4 orders of magnitude higher compared to the other layers in the stack, the voltage drop over the transport layers will usually no longer be observable. The most "power" efficient device will usually be a device, where the voltage is dropped almost only along the emitting layers.

In an embodiment of the present disclosure, the first functional organic layer of the organic electronic device is obtainable (or obtained) by simultaneous evaporation of the copper complex (p-dopant) and the matrix material. The simultaneous evaporation of the copper complex and the matrix material enables an interaction of those molecules.

In an embodiment, the organic electronic device according to the present disclosure can be produced by the following method:

A) providing a substrate,

B) arranging a first electrode on the substrate,

C) arranging at least the first functional organic layer on the first electrode, D) arranging a second electrode on the at least first functional organic layer.

Preferably, the first functional organic layer is produced by simultaneous evaporation of the copper complex according to the present disclosure and the organic compound of the matrix material. Upon evaporation of the copper complex, often dimeric species are observed in the vapor phase. Therefore, complexes with the same type of ligands and the same ligand/copper atom ratio show the same evaporation temperature.

In an embodiment, the electrodes arranged in step B), step D) or in both steps are patterned.

The present disclosure also provides a semiconducting material produced using a copper complex (p-dopant) as described before. Usually this semiconducting material is obtainable by combining a matrix material and the aforesaid copper complex, particularly, by simultaneous evaporation of the matrix material and the copper complex.

Further, the objective of the present disclosure is achieved by a dopant for doping an organic semiconducting matrix material comprising at least two copper atoms, and at least one ligand L bridging the two copper atoms, wherein the ligand L is represented by the following formula:

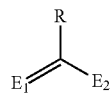

wherein $E_1$ and $E_2$ and R have the meaning as described before. In particular, this polynuclear copper complex is a Lewis-acidic copper complex. According to an embodiment R does not in all coordinated ligands L represent $CF_3$. According to a further embodiment R in none of the ligands L represents $CF_3$.

In a further embodiment the copper complex comprises four, particularly in a "four-membered" ring, or six copper atoms, particularly in a "six-membered" ring, or polymeric species comprising a plurality of copper atoms in a chain-like structure.

In a further embodiment, the polynuclear copper complex contains at least one ligand L (and is, for example, a homoleptic complex) wherein the substituent R of the ligand L contains at least two carbon atoms.

In a further embodiment the copper complex contains a mixed ligand system, for example, a mixture of aliphatic ligands (like trifluoroacetate) and aromatic ligands (like perfluorobenzoate). These mixed systems may, for example, be obtained by partial substitution of the ligands of a homoleptic complex (for example, a homoleptic trifluoroacetate complex).

BRIEF DESCRIPTION OF THE DRAWINGS

Further advantages and advantageous embodiments and developments of the disclosure will become apparent from the embodiments described below in conjunction with the figures.

In the exemplary embodiments and figures, identical or identically acting constituent parts may be provided in each case with the same reference symbols. The elements illustrated and their size relationships among one another should not in principle be regarded as true to scale; rather, individual elements, such as, for example, layers, structural parts, components and regions, may be illustrated with exaggerated thickness or size dimensions for the sake of better representability and/or for the sake of better understanding.

DETAILED DESCRIPTION OF ILLUSTRATIVE EMBODIMENTS

Figure 1:
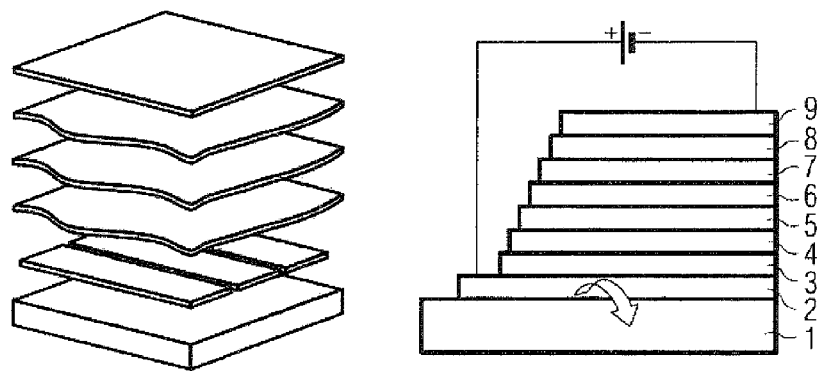
FIG. 1 shows a schematic illustration of a radiation-emitting device according to an embodiment of the disclosure.

FIG. 1 shows a schematic view of one embodiment of the organic electronic device being a radiation emitting device. From the bottom up the following layer sequence is depicted: the bottom most layer is the substrate 1, for example, a transparent substrate, for example, a substrate made of glass. The succeeding layer is an anode layer 2 which may be a transparent conducting oxide (TCO) for example, indium-tin-oxide (ITO). On top of the anode layer 2, a hole-injection layer 3 is arranged. On top of the hole-injection layer, a hole-transport layer 4 is depicted (particularly a hole-transport layer being the first functional organic layer according to the present disclosure containing the p-dopant/copper complex). On top of the hole-transport layer, an emitter layer 5 is arranged. On top of the emitter layer 5, a hole-blocking layer 6 is arranged followed by the electron transport layer 7 and the electron injection layer 8. On top of the electron injection layer, the anode 9 is arranged, for example, an electrode made of metal or a transparent material (giving rise to a top/bottom-emitter).

Upon applying a voltage between anode and cathode, a current flows through the device inducing the release of photons in the emitter layer 5 which leads the radiation emitting device in the form of radiation via the transparent anode 9 and the substrate 1 and/or a transparent cathode. In an embodiment the OLED is emitting white light; the radiation emitting device, therefore, may contain an emitter layer comprising several light emitting materials (for example, blue and yellow or blue, green and red emitting substances); alternatively, several emitter layers comprising molecules emitting light in different colors may be contained. Alternatively a radiation converting material may be contained in the light path.

The OLED shown in FIG. 1 may be produced by sputtering the anode material onto the substrate and subsequently adding the functional layers by evaporation (co-evaporation) of the corresponding materials and/or spin coating.

The device shown in FIG. 1 may also be altered in a way that the layer sequence between anode and cathode is inverted (therefore, the cathode is arranged on the substrate) and a top-emitting device, if non-transparent material is used for the cathode, is obtained.

In more detail, an OLED according to the present disclosure can be obtained by the following procedure.

An ITO pre-structured glass substrate is treated with oxygen plasma for ten minutes and transferred into an evaporator as fast as possible. The evaporator is located inside an argon filled glove-box with oxygen and water concentration being less than 2 ppm. The pressure inside the evaporator is lower than $2 \times 10^{-6}$ mbar.

Two sources, containing the matrix material and the p-dopant are simultaneously heated up to a temperature just below the evaporation temperature. The p-dopant and the matrix materials are then heated up further until a constant evaporation rate is reached. A shutter (inhibiting a deposition of the matrix material and the p-dopant) is opened for the co-evaporation. As a p-dopant, for example, $Cu_2(O_2CCF_3)_4$ and $Cu_4(O_2CCF_3)_4$ may be used. $Cu_2(O_2CCF_3)_4$ is heated up to a temperature of 144° C. yielding in an evaporation rate of 0.14 Å/s; $Cu_4(O_2CCF_3)_4$ is heated up to temperature of 81° C. yielding in an evaporation rate of 0.10 Å/s.

The temperatures for evaporation are strongly dependent on the setup inside the evaporator and the evaporator used for the deposition. The measured temperature, e.g., strongly depends on the position of the thermocouple used for temperature measurements and further setup specifications for every evaporator. All depositions mentioned in this disclosure were done with the same evaporator. The deposition rates can be reproduced easily within a different evaporator due to calibration of sensors.

As matrix materials, for example, the hole-transporting material NPB and the electron transporting material BCP may be used. NPB is heated up to a temperature of 90° C. yielding in an evaporation rate of 2 Å/s; BCP is heated up to a temperature of 74° C. yielding in an evaporation rate of 2 Å/s. Evaporation temperatures and evaporation rates are usually equipment dependent.

Subsequently, the sources are cooled down below 40° C. before the evaporation chamber is vented with argon and opened to change the mask for the cathode deposition. The counter electrode is deposited by thermal evaporation and consists of a 150 nm thick layer of aluminum. The deposition is started (shutter opened) when the evaporation rate reaches 0.5 Å/s and the rate is then increased slowly up to 5 Å/s.

Figure 2:
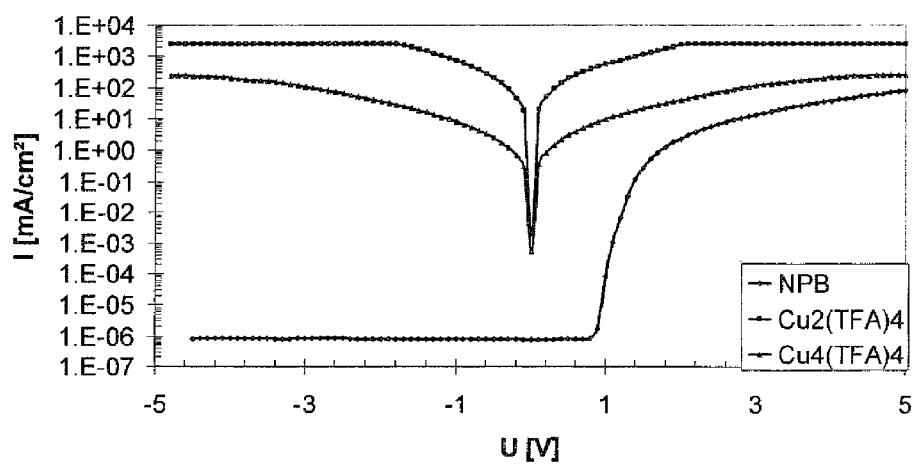
FIG. 2 shows the electrical characteristics of 4 mm² device containing a hole-transport material and the p-dopant according to the present disclosure.
Figure 3:
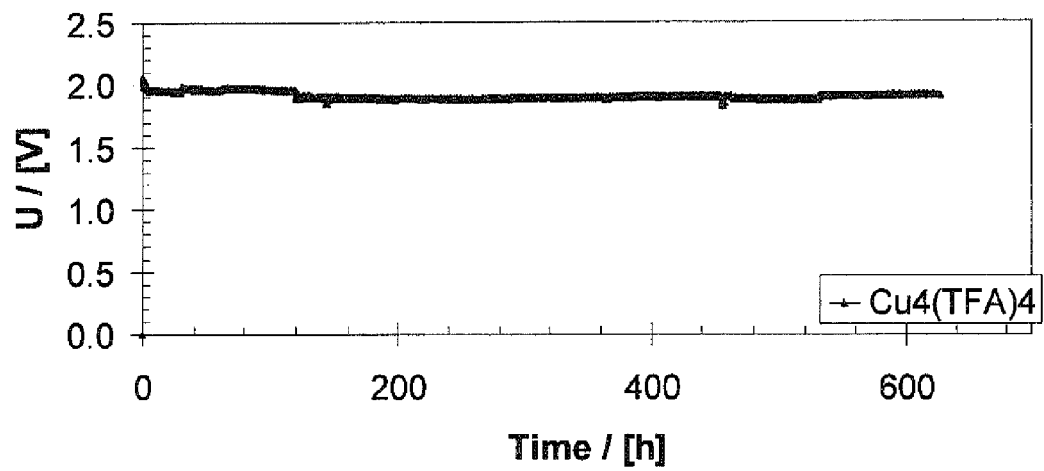
FIG. 3 shows a spectrum indicating the stability of a device used for a spectrum in FIG. 2.
Figure 4:
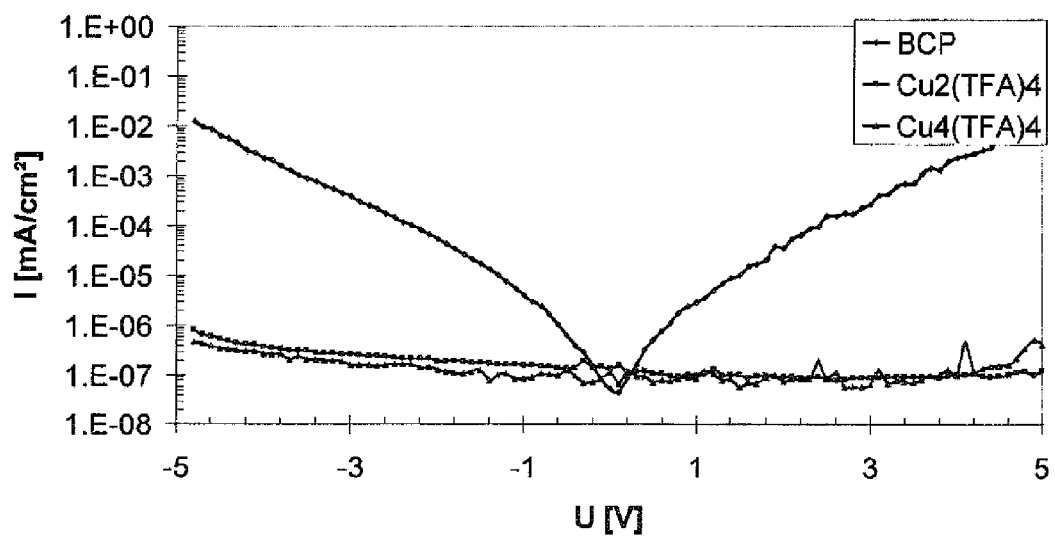
FIG. 4 shows the I-V characteristics of an electron conducting layer doped with the p-dopant of the present disclosure.

The obtained layer sequence is kept inside an inert atmosphere to record the spectrum according to FIGS. 2 to 4 right after the cathode deposition.

FIG. 2 shows a current-voltage (I-V) characteristic of a layer sequence as described before with a 200 nm thick layer of NPB of an 4 mm$^2$ device. The lowest curve in FIG. 2 depicts the electrical characteristic of an undoped NPB layer (diamonds); the curve in the middle is obtained by the same arrangement containing additionally 5% by volume of $Cu_4(O_2CCF_3)_4$ (triangles). The electrical characteristics show enhancement in conductivity by about seven orders of magnitude. In a third experiment there are 200 nm thick layer of NPB is doped with 7% by volume of $Cu_2(O_2CCF_3)_4$ (squares). The electrical characteristics show enhancement in conductivity by about eight orders of magnitude.

Therefore, the present disclosure in general gives rise to an enhancement in conductivity of at least five orders, usually more than seven orders of magnitude compared to an undoped hole-transport layer.

Furthermore, the spectrum depicted in FIG. 2 demonstrates that the injection properties become independent from the work function of the material used for the anode. Aluminum and ITO exhibit the same behavior. Positive voltages indicate hole-injection from ITO, negative voltages from aluminum, respectively.

In FIG. 3 the stability of a device containing a 200 nm thick layer of NPB doped with $Cu_4(O_2CCF_3)_4$. The same device as described above (FIG. 2) was electrically stressed for 700 hours with a current of 1 mA. During the whole testing time the necessary voltage to be applied does not significantly change.

FIG. 4 shows the I-V characteristics of the same layer sequence as described before with the difference that an electron transporting material instead of hole-transporting material is used. For all samples corresponding to FIG. 4 a 200 nm thick layer of BCP was used. BCP is a well known electron conductor. The I-V characteristics of undoped BCP are shown as top most spectrum in FIG. 4 (diamonds). Upon doping the BCP layer with 5% by volume $Cu_4(O_2CCF_3)_4$ (triangles) and 7% by volume $Cu_2(O_2CCF_3)_4$ (squares), respectively, the conductivity of the sample drops to values around the noise level. Therefore, the p-dopants according to the present disclosure do not promote electron conductivity in typical electron conductors, particularly electron conductors based on nitrogen containing aromatic systems; they even prohibit electron conduction.

Figure 5A:
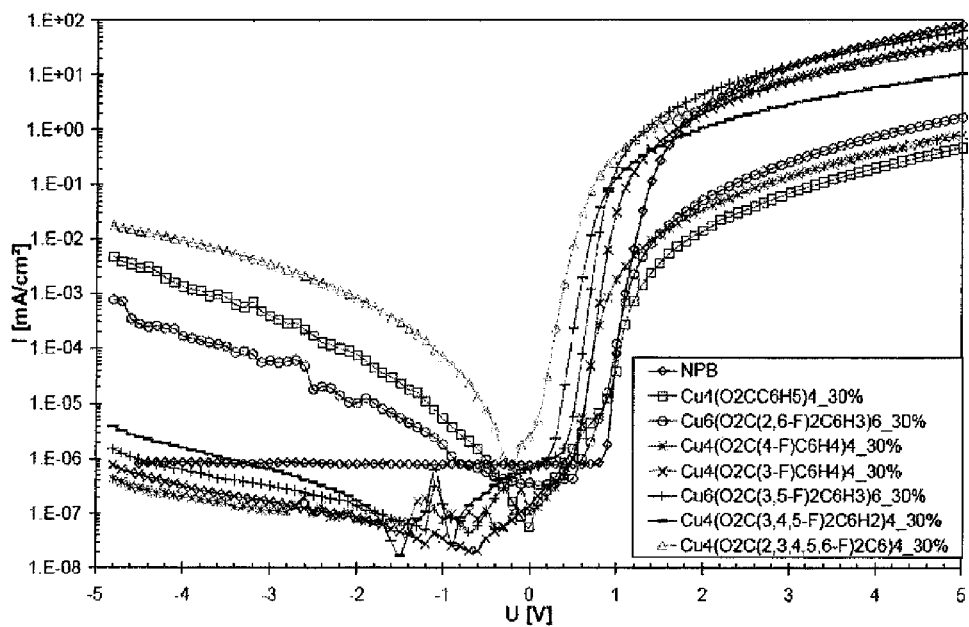
FIG. 5A shows the I-V characteristics of NPB doped with several copper-benzoate complexes.

Seven copper(I)-benzoates were tested as p-dopants in NPB. FIG. 5A shows the I-V characteristics of eight singlecarrier-devices prepared as described before by co-evaporation of NPB and the respective copper complex.

Figure 5B:
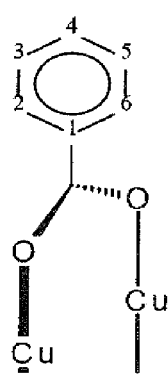
FIG. 5B shows the principle of numbering of the fluorine positions on the benzoic ring of the copper-complex.

Six of these compounds were fluorinated ligand L and the position and quantity of fluorine was varied to investigate the effect on doping. The last compound is non-fluorinated as a kind of reference and to show the difference between fluorinated and non fluorinated complexes. FIG. 5B shows the principle of numbering of the fluorine positions on the benzoic ring of the copper-complex of the seven compounds that have been investigated.

Each device consists of a 200 nm doped organic layer sandwiched between the ITO and aluminum (150 nm) electrodes. Compared to the NPB reference (diamonds) in FIG. 5A, there are two groups of benzoates yielding in different results.

A first group comprises of $Cu_4(O_2CC_6H_5)_4$ (squares), $Cu_6(O_2C(2,6-F)_2C_6H_3)_6$ (circles) and $Cu_4(O_2C(4-F)C_6H_4)_4$ (asterisks) which all show a much lower (3 orders of magnitude) current density for positive voltages compared to NPB and no improvement (drop) of the build-in voltage (no shift towards lower voltages). For the first compound of this group this effect is probably due to the lack of fluorine which seems to be required for a sufficient doping effect. Even though the other two materials contain fluorine, its position and quantity seems to avoid a doping effect. The second compound contains two fluorine atoms on the ring on positions 2 and 6 and are thereby on the "inside" of the compound hindering the electron pulling effect of fluorine and therefore reduce the hole generation possibility on the copper atom and its doping effect. The third compound of this group has one fluorine atom located on position 4 which is on the "outside" of the structure, but the quantity of fluorine is too low to obtain a suitable doping effect.

A second group comprises of four compounds with an increasing quantity of fluorine and a shift of fluorine towards the outer positions of the copper-benzoate structure.

$Cu_4(O_2C(3-F)C_6H_4)_4$ (crosses), $Cu_6(O_2C(3,5-F)_2C_6H_3)_6$ (plusses), $Cu_4(O_2C(3,4,5-F)_3C_6H_2)_4$ (dashes) and $Cu_4(O_2C(2,3,4,5,6-F)_5C_6)_4$ (triangles) all have a similar behavior for positive voltages. The current densities with these materials doped into NPB do not drop by 3 orders of magnitude as for the first group but are within one order of magnitude compared to the NPB reference which is considered to be equivalent. None of those materials increase the current density for higher (4-5 V) positive voltages nor do any of them show a classical symmetrical doping characteristic as copper-trifluoroacetate. However, all of these materials shift the build-in voltage towards lower voltages and thereby increase the current density for lower voltages (0-1 V) and thereby show a kind of doping effect even though it is not as strong as in copper-trifluoroacetate complexes. The factor of position and quantity of fluorine is clearly shown as "outer" positions and more fluorine atoms increase the effect of voltage reduction. Furthermore the best tested material $Cu_4(O_2C(2,3,4,5,6-F)_5C_6)_4$ (triangles) shows a raised characteristic for negative voltages and indicate a possible symmetry which indicates a doping effect. The legend in FIG. 2 is sorted from the reference NPB (top) to the best of the eight tested materials $Cu_4(O_2C(2,3,4,5,6-F)_5C_6)_4$ (bottom).

Figure 6:
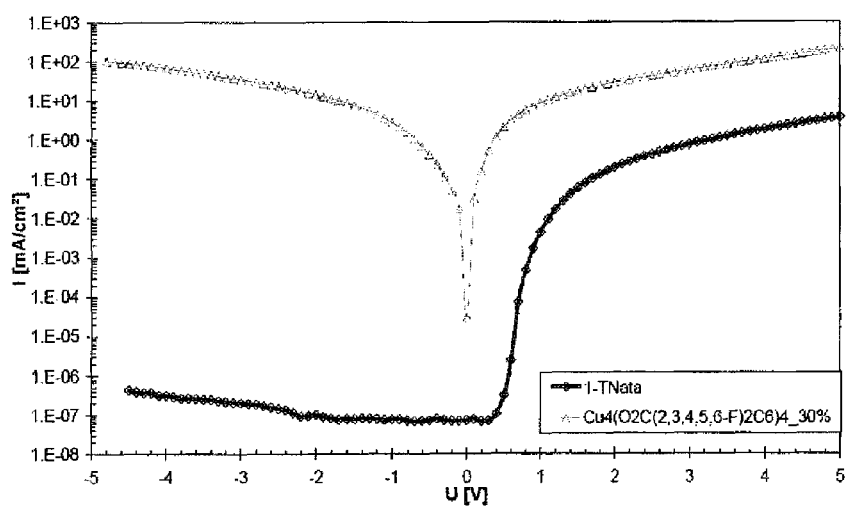
FIG. 6 shows the I-V characteristics of 1-TNata doped with $Cu_4(O_2C(2,3,4,5,6-F)_5C_6)_4$.

Based on these results another test was done to investigate the doping effect of this new group (copper-benzoates) with another matrix material. In general the possibility of doping does not only depend on the dopant, but also on the potential ionization of the matrix material. The lower the HOMO-level (Highest Occupied Molecular Orbital) the easier it is to ionize the material. NPB as the first reference matrix material has a HOMO level of $-5.5$ eV and therefore a material with a lower HOMO was chosen: 1-TNata (4,4',4"-Tris(N-(1-naphthyl)-N-phenyl-amino)triphenylamine) with a HOMO of $-5.0$ eV was used to prepare a similar single carrier device by coevaporation as mentioned before. FIG. 6 shows the I-V characteristics of a single carrier device with 1-TNata doped with $Cu_4(O_2C(2,3,4,5,6-F)_5C_6)_4$ (triangles) and a 1-TNata reference graph (diamonds). As illustrated the characteristic shows an enhancement incurrent density of two orders of magnitude for positive voltages. The symmetrical behavior of this graph (triangles) also shows the independence of the metal work functions of ITO and aluminum. This single carrier device shows a very clear and classical doping effect for the given matrix-dopant combination.

Figure 7:
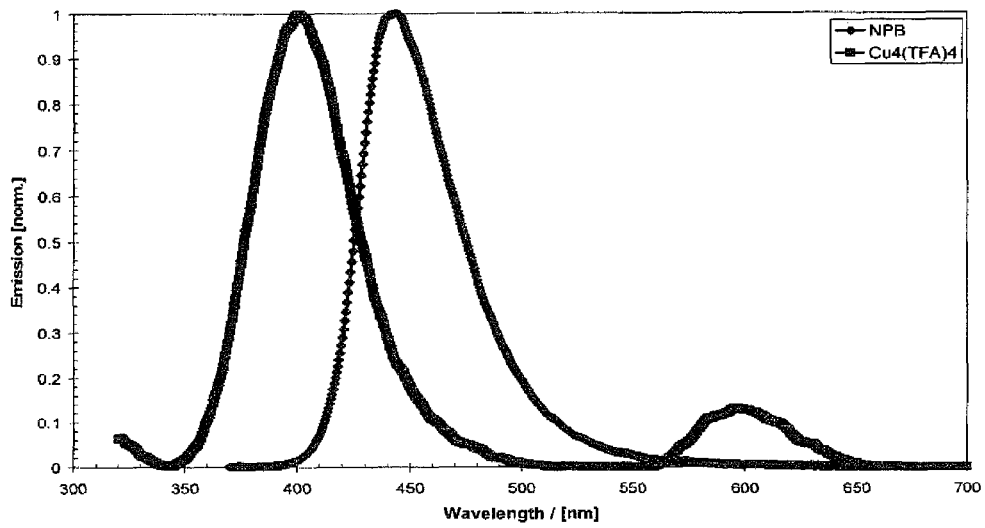
FIG. 7 shows a photoluminescence spectrum of a hole-transport material being undoped or doped with a p-dopant according to the present disclosure.

FIG. 7 shows the photoluminescence spectrum of NPB doped with $Cu_4(O_2CCF_3)_4$. NPB itself exhibits a blue fluorescence with a maximum around 440 nm. The copper complexes according to the present disclosure, particularly the copper(I) trifluoroacetate complex described before, shifts the emission of NPB towards the ultraviolet region. Upon doping NPB with $Cu_4(O_2CCF_3)_4$ the emission maximum of NPB is shifted to around 400 nm. The emission of the copper complex itself is visible at around 580 nm at room temperature (upon excitation with UV radiation, $\lambda_{ex}=350$ nm). In general, the copper(I) complexes according to the present disclosure show an emission maximum between 500 nm and 600 nm. In the following examples for the preparation of the copper complexes according to the present disclosure are described:

1. General Synthesis Starting from Copper(I) Oxide $Cu_2O$ and an anhydride of the respective carboxylic acid (in excess, for example, two-fold excess with respect to a molar ratio of copper:carboxylic acid of 1:1) mixed with a suitable solvent and refluxed over night. $Cu_2O$ having not reacted is removed by filtration. The solvent is evaporated and the obtained material heated under vacuum at elevated temperature for at least ten hours. The obtained material may be purified by sublimation.

If no anhydride of the carboxylic acid is available, also the carboxylic acid itself and water trapping material (for example, DEAD) may be used.

2. Synthesis of Unligated $Cu_4(O_2CCF_3)_4$ $Cu_2O$ (0.451 g, 3.15 mmol) was added and 2 ml of $(CF_3CO)_2O$, followed by 30 ml of benzene. The mixture was refluxed over night to give a blue solution and some unreacted starting material. This suspension was filtered through celite to remove the $Cu_2O$. The blue solution was then evaporated to dryness, affording a very pale blue solid. It was heated at 60° C. to 70° C. under vacuum for 10 to 15 hours to give the desired product. Yield: 64%. Crystalline material is obtained by sublimation of the crude solid at 110° C. to 120° C.

3. Synthesis of $Cu_4(O_2CC_6H_5)_4$

Benzoic acid (2.5 g, 10.24 mmol) was heated under nitrogen for two hours in refluxing xylenes (14 ml) in a Dean-Stark apparatus. The obtained solution was added to a copper (I) oxide (0.2 g, 1.40 mmol) and reflux was continued until all the oxide had reacted (approximately 12 hours). Upon slow cooling to room temperature, the product started to appear as a white crystalline precipitate while benzoic acid remained in the solution. After two and a half hours and thirteen minutes the solution was removed by a canula. The polycrystalline powder was washed with xylenes (3 times 20 ml) and dried under vacuum. Yield: 75%.

In this example a Dean-Stark apparatus is used instead of a water trapping material.

4. General Synthesis of Copper(I) Complexes Starting from $Cu_4(O_2CCF_3)_4$ $Cu_4(O_2CCF_3)_4$ and an at least five-fold excess of a carboxylic acid to be coordinated to the copper atoms are combined with a suitable solvent and refluxed for at least 12 hours. The obtained solution is evaporated to dryness and heated at elevated temperature under vacuum for several days to remove the excess of unreacted acid. Pure product may be obtained by sublimation.

5. Synthesis of $Cu_4(O_2C(3-F)C_6H_4)_4$ $Cu_4(O_2CCF_3)_4$ (0.797 g, 1.13 mmol) (3-F)$C_6H_4$COOH (0.945 g, 6.75 mmol) are loaded in a Schlenk flask inside a glove box and 55 ml of benzene was added to the mixture. A homogenous light blue solution was refluxed over night and then evaporated to dryness to afford a very pale blue solid. It was heated at 90° C. to 100° C. under vacuum for several days to remove the excess of unreacted acid. Air stable colorless blocks were obtained by sublimation-deposition of the crude powder at 220° C. in one week. Yield: 65%.

6. Synthesis of Unligated $Cu_2(O_2CCF_3)_4$

Commercially available $Cu(O_2CCF_3)_2$*n $H_2O$ (0.561 g, 1.94 mmol) was dissolved in 3 ml of acetone to give an intensely blue suspension. Filtration and removal of all volatiles under reduced pressure afforded a blue-green residue, which was kept under a dynamic vacuum at 70° C. to 80° C. for 34 hours to give a green solid. Yield: 87%.

7. General Synthesis Starting from Copper(II) Oxide

Alternative A) Copper(II) oxide is reacted with an excess of a corresponding acid (for example, pivalic acid, HOOCC$(CH_3)_3$)) upon heating (molar ratio, for example, Cu:HL=1:5). A crystalline product precipitates after the solution is allowed to cool down. The solids are then filtered and dried. They may, contain coordinated carboxylic acids, but recrystallization from anhydrous acetone followed by drying under vacuum, as described in example 7, yields unligated copper (II) carboxylates (see also S. I. Troyanov et al., Koord. Khimijya, 1991, vol 17, N12, 1692-1697).

Alternative B)—electrochemical synthesis of copper(II) carboxylates according to K. Kushner et al., J. Chem. Ed. 2006, 83, 1042-1045.

8. Synthesis of $Cu_6(O_2C(2,4-F)_2C_6H_3)_6$.

A mixture of $Cu_4(O_2CCF_3)_4$ (0.75 g, 4.2 mmol) and 2,4-difluorobenzoic acid (0.840 g, 5.3 mmol) was loaded in a glove box into a 100 ml Schlenk flask. Then 50 ml of benzene was added to the flask. The reaction mixture was refluxed for 24 hours to afford a light blue solution with a white precipitate. The product was filtered off and washed with benzene (three times 10 ml). It was then heated under reduced pressure at 80° C. to 90° C. for two to three days. The resulting solid was loaded into a small glass ampoule, which was evacuated and sealed under vacuum. Crystals were obtained as small colorless blocks by sublimation-deposition procedures from the gas phase at 160° C.-190° C. Yield (single crystalline material): 0.439 g (47%).

Figure 8:
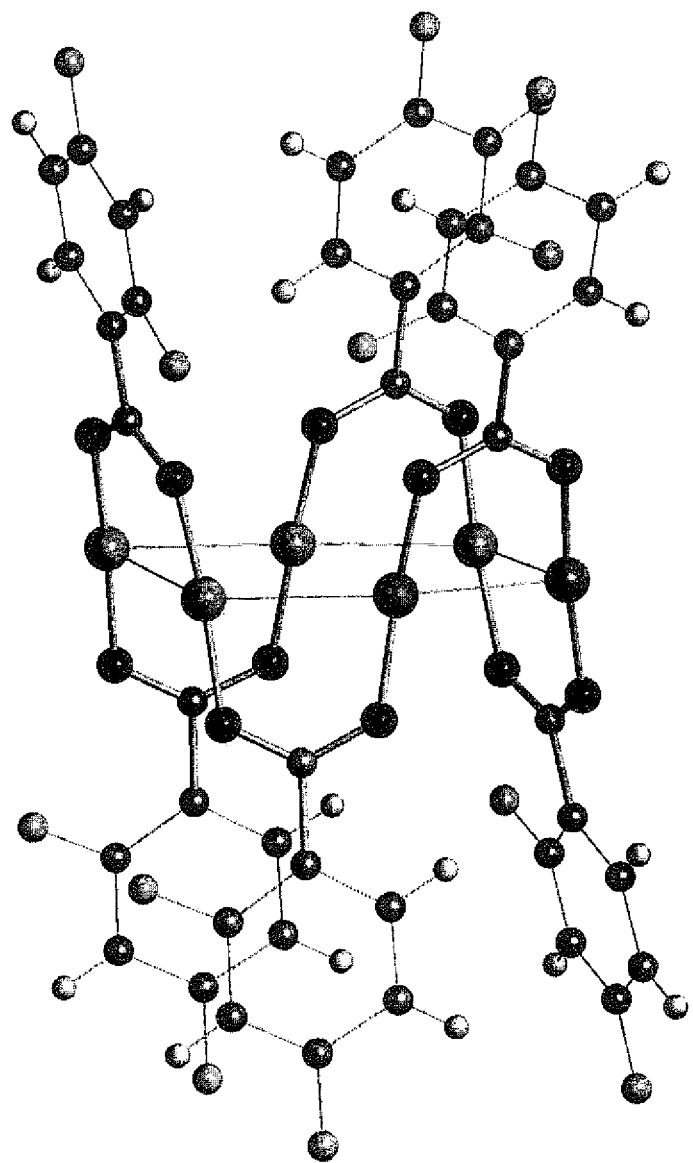
FIG. 8 shows an x-ray structure of the compound $Cu_6(O_2C(2,4-F)_2C_6H_3)_6$.

FIG. 8 shows an X-ray structure of this compound. The lines between the copper atoms do not represent copper-copper bonds.

The invention is not restricted by the description on the basis of the exemplary embodiments. Rather, the invention encompasses any new feature and any combination of features, which, in particular, comprises any combinations of features in the patent claims, even if this feature or this combination itself is not explicitly explained in the pattern claims for exemplary embodiments.

What is claimed is:

1. An organic electronic device, comprising:
a substrate;
a first electrode arranged on the substrate;
at least a first functional organic layer arranged on the first electrode; and
a second electrode arranged on the first functional organic layer,
wherein the first functional organic layer comprises a matrix material and a p-dopant with regard to the matrix material, wherein the p-dopant comprises a Lewis-acidic copper complex containing at least one ligand L of the following formula:

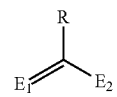

wherein E1 and E2 may be the same or different and represent oxygen, sulphur, selenium or NR', wherein R represents hydrogen or a substituted or unsubstituted, branched, linear or cyclic hydrocarbon, and wherein R' represents hydrogen or a substituted or unsubstituted, branched, linear or cyclic hydrocarbon.

2. The organic electronic device according to claim 1, wherein the Lewis-acidic copper complex is a polynuclear complex.

3. The organic electronic device according to claim 2, wherein the at least one ligand L of the Lewis-acidic copper complex is bridging two copper atoms.

4. The organic electronic device according to claim 1, wherein copper atoms contained in the Lewis-acidic copper complex are at least partially in an oxidation state +2.

5. The organic electronic device according to claim 1, wherein a copper atom or copper atoms contained in the Lewis-acidic copper complex are at least partially in an oxidation state +1.

6. The organic electronic device according to claim 1, wherein the group R of the at least one ligand L represents an alkyl and/or aryl group bearing at least one electron withdrawing substituent.

7. The organic electronic device according to claim 1, wherein the first functional organic layer is a hole transport layer.

8. The organic electronic device according to claim 1, wherein the first functional organic layer is an electron blocking layer.

9. The organic electronic device according to claim 1, wherein the matrix material of the first functional organic layer comprises an organic compound and the organic compound partially coordinates to the Lewis-acidic copper complex.

10. The organic electronic device according to claim 9, wherein the organic compound contains at least two coordination sites and wherein the at least two coordination sites of at least a part of the organic compound coordinate to a copper atom so as to form a catenarian structure or a netlike structure of a plurality of Lewis-acidic copper complexes and a plurality of molecules of the organic compound.

11. The organic electronic device according to claim 1, wherein the organic electronic device comprises a device selected from the group consisting of a field effect transistor, a solar cell, a photo detector, an optoelectronic component, a light-emitting diode and a display.

12. The organic electronic device according to claim 1, wherein the first functional organic layer is obtainable by simultaneous evaporation of the Lewis-acidic copper complex and the matrix material.

13. The organic electronic device according to claim 1, wherein the conductivity of holes in the matrix material with the p-dopant is at least seven orders of magnitude more than in an undoped matrix material.

14. An organic electronic device, comprising:
- a substrate;
- a first electrode arranged on the substrate;
- at least a first functional organic layer arranged on the first electrode; and
- a second electrode arranged on the first functional organic layer,
- wherein the first functional organic layer comprises a matrix material and a p-dopant with regard to the matrix material, wherein the first functional organic layer comprises a hole transport layer, wherein the p-dopant comprises a Lewis-acidic copper complex containing at least one ligand L of the following formula:

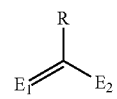

wherein E1 and E2 may be the same or different and represent oxygen, sulphur, selenium or NR', wherein R represents hydrogen or a substituted or unsubstituted, branched, linear or cyclic hydrocarbon, and wherein R' represents hydrogen or a substituted or unsubstituted, branched, linear or cyclic hydrocarbon, wherein the conductivity of holes in the matrix material with the p-dopant is at least five orders of magnitude more than the conductivity of holes in the matrix material with no p-dopant.

* * * * *

UNITED STATES PATENT AND TRADEMARK OFFICE
CERTIFICATE OF CORRECTION

| | | |
|---|---|---|
| PATENT NO. | : 8,624,229 B2 | Page 1 of 1 |
| APPLICATION NO. | : 12/884683 | |
| DATED | : January 7, 2014 | |
| INVENTOR(S) | : Guenter Schmid | |

It is certified that error appears in the above-identified patent and that said Letters Patent is hereby corrected as shown below:

On the Title Page, Item (75) Inventors, line 2, delete "Nuremberg (DE)" and insert
--Nuernberg (DE)--.

Signed and Sealed this
Fourth Day of March, 2014

Michelle K. Lee
*Deputy Director of the United States Patent and Trademark Office*